United States Patent
Thevenier et al.

(10) Patent No.: US 11,109,616 B2
(45) Date of Patent: Sep. 7, 2021

(54) METHOD FOR PRODUCING A NUTRITIONAL COMPOSITION

(71) Applicant: NESTEC S.A., Vevey (CH)

(72) Inventors: Anne Thevenier, Bern (CH); Susanne Schuh, Gumlingen (CH); Martinas Kuslys, Grosshoechstetten (CH); Rinat Ran-Ressler, Bridgewater, NJ (US); Koraljka Rade-Kukic, Lafayette, CA (US)

(73) Assignee: Societe des Produits Nestle S.A., Vevey (CH)

( * ) Notice: Subject to any disclaimer, the term of this patent is extended or adjusted under 35 U.S.C. 154(b) by 132 days.

(21) Appl. No.: 16/331,800

(22) PCT Filed: Sep. 13, 2017

(86) PCT No.: PCT/EP2017/073040
§ 371 (c)(1),
(2) Date: Mar. 8, 2019

(87) PCT Pub. No.: WO2018/050704
PCT Pub. Date: Mar. 22, 2018

(65) Prior Publication Data
US 2019/0364950 A1    Dec. 5, 2019

Related U.S. Application Data

(60) Provisional application No. 62/393,787, filed on Sep. 13, 2016.

(51) Int. Cl.
*A23L 33/185* (2016.01)
*A23L 33/18* (2016.01)
*A23L 33/115* (2016.01)
*A23L 33/16* (2016.01)
*A23L 33/125* (2016.01)
(Continued)

(52) U.S. Cl.
CPC ............... *A23L 33/185* (2016.08); *A23L 3/46* (2013.01); *A23L 33/115* (2016.08); *A23L 33/125* (2016.08); *A23L 33/16* (2016.08); *A23L 33/18* (2016.08); *A23L 33/40* (2016.08); *A23V 2002/00* (2013.01)

(58) Field of Classification Search
CPC ...... A23L 33/18; A23L 33/185; A23L 33/125; A23L 33/40; A23L 33/115; A23L 33/16; A23L 3/46; A61P 37/08; A23V 2250/548; A23V 2200/304; A23V 2002/00; A23V 2200/00
See application file for complete search history.

(56) References Cited

U.S. PATENT DOCUMENTS

| 2013/0243904 A1 | 9/2013 | Cordle et al. |
| 2015/0305359 A1 | 10/2015 | Ao et al. |
| 2016/0037817 A1 | 2/2016 | Johns et al. |

FOREIGN PATENT DOCUMENTS

| WO | 2015089009 | 6/2015 |
| WO | 2015187817 | 12/2015 |

*Primary Examiner* — Subbalakshmi Prakash
(74) *Attorney, Agent, or Firm* — K&L Gates LLP (57) ABSTRACT

A method for producing a nutritional composition comprising the steps: (a) providing a solution comprising at least one mineral for a nutritional composition; (b) adding at least one potato protein to the solution of step (a); (c) adding at least one carbohydrate and/or at least one fat to the solution of step (b); and (d) spray drying the solution of step (c).

17 Claims, 7 Drawing Sheets

(51) Int. Cl.
*A23L 33/00* (2016.01)
*A23L 3/46* (2006.01)

METHOD FOR PRODUCING A NUTRITIONAL COMPOSITION

CROSS REFERENCE TO RELATED APPLICATIONS

The present application is a National Stage of International Application No. PCT/EP2017/073040, filed on Sep. 13, 2017, which claims priority to U.S. Provisional Application No. 62/393,787, filed on Sep. 13, 2016, the entire contents of which are being incorporated herein by reference.

FIELD OF THE INVENTION

The present invention relates to nutritional compositions and methods for their production. In particular, the invention relates to infant formulas that are suitable for subjects with cow's milk protein allergy.

BACKGROUND TO THE INVENTION

Human breast milk and breast feeding are considered to be the optimal form of nutrition for healthy infants during the first months of life. However, there is a need for nutritional sources that can be used in addition to breast milk. Furthermore, not all infants can be breast fed and the needs of more vulnerable infants, such as preterm infants, cannot be achieved by their mother's milk, so there is also a need for alternatives to breast milk.

Nutritional compositions that satisfy the nutritional requirements of infants may be used as a substitute for or complement to human breast milk. Preferably, infant formulas should have an acceptable taste, and be hypoallergenic when targeted to infants who are allergic or at risk of allergy.

Infant formulas are typically formulated with cow's milk protein. For example, bovine whey protein and/or casein are often used as the protein source in infant formulas. However, some infants exhibit an allergy to cow's milk proteins, making such formulas unsuitable. Allergies to cows' milk and to infant formulas containing cow's milk protein may be due to the differences between the proteins in cows' milk and those in human milk. The principal recognised cow's milk allergens are alpha-lactalbumin (aLA), beta-lactoglobulin (bLG) and bovine serum albumin (BSA).

To reduce allergenicity, cow's milk proteins may be hydrolysed (e.g. enzymatically) either partially, or in the case of products intended for the management of Cow's Milk Protein Allergy (CMPA), extensively. However, such proteins must be highly processed to provide sufficient hydrolysis to reduce the risk of an allergic reaction. Such processing may be viewed unfavourably with an increasing tendency to provide more natural diets and a strong hydrolysis process also tends to have a negative impact on taste. In addition, the extensive processing increases the cost of the product formulas.

Alternatives to cow's milk protein may be used in nutritional compositions, for example soy and rice proteins. However, soy-based nutritional compositions are not recommended by the European Society for Paediatric Gastroenterology, Hepatology and Nutrition (ESPGHAN) for infants (0-12 months), because of the risk of a cross allergic response. Rice-based nutritional compositions require the addition of numerous free amino acids to provide the correct amino acid profile for infant formulas, due to the incomplete natural amino acid distribution in rice proteins. This increases cost and may provide the resulting formula with a less palatable taste. Furthermore, rice proteins are generally insoluble and require at least partial hydrolysis for solubilisation.

Infant formulas may be formulated entirely from free amino acids for infants with severe cases of multiple allergies. However, ESPGHAN guidelines indicate that such formulas should not be used as a first line solution in the case of cow's milk protein allergic infants. Furthermore, overprescription of amino acid based formulas adds to the cost burden on national health systems as amino acid based formulas are even more expensive than extensively hydrolysed formulas. Accordingly, there is a significant need for nutritional compositions, such as infant formulas, that comprise less potential allergens, and preferably which require minimal processing, have good taste and have low cost. In particular, there is a need for nutritional compositions, such as infant formulas, that are suitable for administration to subjects with cow's milk protein allergy.

SUMMARY OF THE INVENTION

The inventors have developed a nutritional composition based on potato protein as the major protein source, which is naturally absent in the major allergens found in milk and soy. Accordingly, the nutritional composition may provide a naturally hypoallergenic nutritional composition (e.g. infant formula) that is suitable for subjects with cow's milk protein allergy.

In particular, the inventors have developed an improved process for the production of potato protein-based nutritional compositions, which provides improvements such as reduced viscosity during processing. The viscosity reduction during processing increases the ease of spray-drying to form a powdered product, for example.

The inventors surprisingly found that the order of the addition of the minerals has a significant effect on the viscosity of the liquid product. Optimising this order makes it possible to achieve viscosities which improve spray drying and the quality of the spray-dried powder product. For example, the inventors found that adding some minerals to the solution before the potato protein and some after was beneficial, as was adding all minerals before the protein.

In addition, the inventors have found potato protein to have a well-balanced amino acid profile, which is closer to that of human milk than rice or soy protein. Accordingly, less addition of free amino acids is required to provide a composition with the required nutritional profile, which renders the resulting product more cost effective and gives it a more palatable taste.

As a result of their lower allergen profile, the potato protein components do not require extensive hydrolysis, which provides significant benefits in terms of cost and for the development of an infant, because the intact or slightly hydrolysed proteins facilitate improved gut maturation.

In addition, use of potato protein provides for good acceptance, for example in terms of taste and texture of the nutritional composition.

Accordingly, in one aspect the invention provides a method for producing a nutritional composition comprising the steps:
(a) providing a solution comprising at least one mineral for a nutritional composition;
(b) adding at least one potato protein to the solution of step (a);
(c) adding at least one carbohydrate and/or at least one fat to the solution of step (b); an
(d) spray drying the solution of step (c). d In one embodiment, the solution is stirred during steps (a) and/or (b). Preferably, the solution is stirred to dissolve and/or hydrate the protein, carbohydrate and/or fat. For example, the solution may be stirred during steps (a) and/or (b) for about 0.5-3.0 h or 0.5-1.5 h, preferably 0.5-1.5 h.

In one embodiment, the solution (e.g. the solution of steps (a)-(d)) is maintained at an acidic pH (i.e. a pH below 7). In one embodiment, the solution (e.g. the solution of steps (a)-(d)) is maintained at a pH of about 3.8-7.0, 4.0-7.0, 5.0-7.0, 6.0-7.0, 6.2-6.8 or 6.4-6.8, preferably about 6.4-6.8. In another preferred embodiment, the solution (e.g. the solution of steps (a)-(d)) is maintained at a pH of about 3.8-4.2. Any additional steps for hydrolysis of the potato protein may be carried out at a different pH.

In one embodiment, step (a) further comprises adjusting the pH of the solution to about 3.8-7.0, 4.0-7.0, 5.0-7.0, 6.0-7.0, 6.2-6.8 or 6.4-6.8, preferably about 6.4-6.8, before addition of the at least one potato protein in step (b). In another preferred embodiment, step (a) further comprises adjusting the pH of the solution to about 3.8-4.2 before addition of the at least one potato protein in step (b).

In one embodiment, step (c) further comprises adjusting the pH of the solution to about 3.8-7.0, 4.0-7.0, 5.0-7.0, 6.0-7.0, 6.2-6.8 or 6.4-6.8, preferably about 6.4-6.8, after addition of the at least one carbohydrate, and preferably before addition of the at least one fat. In another preferred embodiment, step (c) further comprises adjusting the pH of the solution to about 6.0-6.4 after addition of the at least one carbohydrate, and preferably before addition of the at least one fat.

In one embodiment, the product nutritional composition is at a neutral or acidic pH, for example a pH of about 3.8-7.0, 4.0-7.0, 5.0-7.0, 6.0-7.0, 6.2-6.8, 6.4-6.8 or 6.0-6.4.

In one embodiment, step (c) comprises adding the at least one carbohydrate before the at least one fat.

In one embodiment, the solution is at a temperature of about 55-65° C. or 55-60° C., preferably 55-60° C., during admixing of the minerals, protein and carbohydrate of steps (a)-(c).

In one embodiment, the solution of step (c) has total solids of about 35-45% before addition of the fat.

In one embodiment, the solution of step (c) has total solids of about 40-55% after addition of the fat.

In a preferred embodiment, the method does not comprise a homogenisation step. Preferably, the solution of step (c) is not homogenised before the spray drying of step (d). Not applying a homogenisation step provides further improvements to the method by reducing viscosity of the solution before spray drying.

In another embodiment, the method further comprises a homogenisation step. Preferably, the solution of step (c) is homogenised before the spray drying of step (d).

In one embodiment, the solution is at a temperature of at least about 75° C., for example 75-90° C., 75-85° C. or 75-80° C. during the homogenisation.

In one embodiment, the fat is added after the temperature is increased to at least about 75° C., for example 75-90° C., 75-85° C. or 75-80° C. In another embodiment, the fat is added before the temperature is increased to at least about 75° C., for example 75-90° C., 75-85° C. or 75-80° C.

In one embodiment, the homogenisation is carried out at a pressure of about 200-350 bar.

In one embodiment, the homogenisation is carried out in a single step, preferably at a pressure of about 10-100 bar.

In another embodiment, the homogenisation is carried out in two steps. Preferably, the first homogenisation step is at a pressure of about 50-250 bar and the second homogenisation step is at a pressure of about 20-150 bar.

In a preferred embodiment, the nutritional composition is an infant formula.

In one embodiment, the at least one mineral of step (a) comprises calcium citrate and/or potassium citrate, and optionally sodium citrate and/or potassium phosphate monobasic. In another embodiment, the at least one mineral of step (a) further comprises magnesium chloride, magnesium oxide, calcium chloride, calcium glycerophosphate, sodium chloride, calcium phosphate, potassium hydroxide and/or sodium hydroxide.

In one embodiment, the at least one mineral of step (a) comprises calcium citrate, potassium citrate and/or potassium phosphate monobasic, and optionally sodium citrate, magnesium chloride, magnesium oxide, calcium chloride, calcium glycerophosphate, sodium chloride, calcium phosphate, potassium hydroxide and/or sodium hydroxide.

In one embodiment, the at least one mineral of step (a) comprises calcium citrate, potassium citrate, potassium phosphate monobasic, sodium citrate, magnesium chloride, magnesium oxide, calcium chloride, calcium glycerophosphate, sodium chloride, calcium phosphate, potassium hydroxide and sodium hydroxide.

In one embodiment, step (c) further comprises adding at least one vitamin, preferably after addition of the at least one carbohydrate, and preferably before addition of the at least one fat.

In one embodiment, step (c) further comprises adding at least one mineral, preferably after addition of the at least one carbohydrate, and preferably before addition of the at least one fat.

In one embodiment, the minerals added during step (a) are not added again during step (c).

In one embodiment, the at least one mineral added in step (c) comprises magnesium chloride, magnesium oxide, calcium chloride, calcium glycerophosphate, potassium phosphate monobasic, sodium chloride, calcium phosphate, sodium citrate, sodium hydroxide and/or potassium hydroxide.

In a preferred embodiment, the major source of protein is potato protein.

In a particularly preferred embodiment, the nutritional composition does not comprise dairy protein.

In a preferred embodiment, the major source of protein in the nutritional composition is potato protein and the remaining protein is plant protein.

The term "major source of protein is potato protein" means that the largest fraction of the total protein by weight in a composition originates from potato protein.

In one embodiment, at least about 50%, 55%, 60%, 65%, 70%, 75%, 80%, 85%, 90% or 95%, preferably at least about 75%, by weight of the total protein in the nutritional composition is potato protein.

In a preferred embodiment, 100% by weight of the total protein in the nutritional composition is potato protein.

In a preferred embodiment, the protein (in particular, the potato protein) is intact protein. Preferably, the protein has not been subjected to artificial hydrolysis.

In one embodiment, the potato protein is hydrolysed potato protein. In one embodiment, the protein (in particular, the potato protein) is partially hydrolysed protein. In one embodiment, the protein (in particular, the potato protein) is extensively hydrolysed protein.

In one embodiment, the method further comprises producing the hydrolysed potato protein by a method comprising the steps:
(i) providing a solution comprising potato protein, and optionally adjusting the pH of the solution to about 5.0-8.0, 5.0-7.6, 5.0-7.4, 6.0-7.6, 7.0-7.6 or 7.2-7.6, preferably 7.2-7.6;
(ii) adding a protease, preferably alcalase, to the solution of step (i);
(iii) incubating the solution of step (ii) under conditions suitable for hydrolysis of the potato protein; and
(iv) inactivating the protease.

In one embodiment, the incubation of step (iii) comprises adding the protease to provide an enzyme:substrate ratio of about 0.5-5% by weight.

In one embodiment, the incubation of step (iii) comprises incubating the solution at a temperature of about 50-70° C. or 55-60° C., preferably 55-60° C.

In one embodiment, the incubation of step (iii) is for about 0.5-5 h.

In one embodiment, the inactivation of step (iv) comprises heating the solution to about 85-95° C. or 88-92° C., preferably 88-92° C. Preferably, the solution is heated for at least about 5 minutes, for example about 5-30, 5-20, 5-15 or 5-10 minutes. Preferably, the solution is cooled to about 55-65° C. or 55-60° C., preferably 55-60° C., after the inactivation of step (iv).

In one embodiment, the solution comprising potato protein of step (i) has about 9-16% total protein solids.

In one embodiment, the nutritional composition further comprises free amino acids.

In one embodiment, the nutritional composition does not comprise a further emulsifier. The potato protein may provide sufficient function as an emulsifier.

In one embodiment, the nutritional composition (e.g. the infant formula) further comprises lactose (i.e. the carbohydrate may comprise lactose). In one embodiment, the nutritional composition (e.g. the infant formula) does not comprise lactose.

In one embodiment, the nutritional composition (e.g. the infant formula) further comprises maltodextrin (i.e. the carbohydrate may comprise maltodextrin). In one embodiment, the nutritional composition (e.g. the infant formula) does not comprise maltodextrin.

In one embodiment, the nutritional composition (e.g. the infant formula) further comprises lactose and maltodextrin (i.e. the carbohydrate may comprise lactose and maltodextrin).

In one embodiment, the nutritional composition (e.g. the infant formula) is for a subject (e.g. an infant) with cow's milk protein allergy.

In one embodiment, the nutritional composition (e.g. the infant formula) further comprises probiotics. In one embodiment, the nutritional composition (e.g. the infant formula) does not comprise probiotics.

In one embodiment, the infant formula further comprises nucleotides. In one embodiment, the infant formula does not comprise nucleotides.

In one embodiment, the infant formula comprises:
(a) 1.8-3.2 g protein per 100 kcal;
(b) 9-14 g carbohydrate per 100 kcal; and
(c) 4.0-6.0 g lipids per 100 kcal.

In another aspect, the invention provides a nutritional composition obtainable by the method of the invention.

In another aspect, the invention provides a method for feeding a subject comprising administering to the subject the nutritional composition of the invention.

In a preferred embodiment, the subject is an infant. Particularly preferably, the subject has cow's milk protein allergy.

In another aspect, the invention provides the nutritional composition of the invention for use in feeding a subject, preferably an infant, having cow's milk protein allergy.

DETAILED DESCRIPTION OF THE INVENTION

Various preferred features and embodiments of the present invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

Allergy

The term "allergy" refers to a hypersensitivity of the immune system to a substance which is normally tolerated. The allergy may be an allergy detected by a medical doctor.

The term "food allergy" refers to an allergy with respect to a nutritional composition.

Infant formulas are typically formulated with cow's milk protein. For example, bovine whey protein and/or casein are often used as the protein source in infant formulas. However, some infants exhibit an allergy to cow's milk proteins, making such formulas unsuitable.

In addition to infants, older subjects (e.g. older children) may suffer from cow's milk protein allergy.

Allergies to cows' milk and to infant formulas containing cow's milk protein may be due to the differences between the proteins in cows' milk and those in human milk. The principal recognised cow's milk allergens are alpha-lactalbumin (aLA), beta-lactoglobulin (bLG) and bovine serum albumin (BSA).

Subjects

The subjects referred to in the present disclosure as the target of the nutritional compositions disclosed herein are human subjects.

In a preferred embodiment, the subjects are infants.

The term "infant" refers to a child under the age of 12 months, for example a child between 0 and 6 months of age.

In another embodiment, the subjects are 12-36 months of age. The nutritional compositions of the invention that may be used for such subjects may be follow on formulas.

Nutritional Composition

The term "nutritional composition" refers to a composition that provides nutrition. The composition preferably includes protein, carbohydrate, fat and/or other components (e.g. vitamins and minerals) useful for nutrition of a subject. The levels of the individual components in a nutritional composition may be selected so as to provide tailored nutritional intake for an individual.

In a preferred embodiment, the nutritional composition is an infant formula.

In another embodiment, the nutritional composition is a follow on formula.

Infant Formula

The term "infant formula" may refer to a foodstuff intended for particular nutritional use by infants during the first year of life and satisfying by itself the nutritional requirements of this category of person, as defined in European Commission Directive 2006/141/EC of 22 Dec. 2006.

Infants can be fed solely with infant formulas or the infant formula can be used as a complement of human milk.

The term "infant formula" includes hypoallergenic infant formulas. A hypoallergenic composition is a composition which is unlikely to cause allergic reactions.

The infant formula of the invention may be in the form of a powder or liquid. The liquid may be, for example, a concentrated liquid infant formula or a ready-to-feed formula. The infant formula may be in the form of a reconstituted infant formula (i.e. a liquid infant formula that has been reconstituted from the powdered form). Preferably, the infant formula is in the form of a powder.

The powder is preferably capable of being reconstituted into a liquid composition suitable for feeding an infant, for example by the addition of water. Similarly, the concentrated liquid infant formula is preferably capable of being diluted into a liquid composition suitable for feeding an infant, for example by the addition of water.

In one embodiment, the infant formula has an energy density of about 60-70 kcal per 100 mL, when formulated as instructed.

Protein

The term "protein" refers to polymers of amino acids, and includes polypeptides and peptides. The term "protein" does not encompass free amino acids, which may also be present in the nutritional composition (e.g. infant formula) of the invention.

The protein content of the infant formula of the invention is preferably in the range 1.8-3.2 g protein per 100 kcal. In a preferred embodiment, the protein content of the infant formula of the invention is in the range 1.8-2.8 g protein per 100 kcal.

The nutritional composition (e.g. infant formula) of the invention comprises potato protein as the major protein source. In one embodiment, at least about 50%, 55%, 60%, 65%, 70%, 75%, 80%, 85%, 90% or 95%, preferably at least about 75%, more preferably 100%, by weight of the total protein in the nutritional composition is potato protein.

The remaining protein in the nutritional composition of the invention may be any protein which is suitable for use in a nutritional composition, in particular an infant formula.

Preferably, the nutritional composition does not comprise dairy protein. Accordingly, in a preferred embodiment 100% by weight of the total protein in the nutritional composition is non-dairy protein.

In a preferred embodiment, 100% by weight of the total protein in the nutritional composition is plant protein.

Example plant proteins that may optionally be used in the nutritional composition disclosed herein, in addition to the potato protein, include pea, rice, quinoa, oat, sunflower, or coconut proteins, or combinations thereof.

Further example non-dairy proteins for use in the nutritional composition disclosed herein include algal protein or leaf protein.

In a preferred embodiment, the major source of protein in the infant formula is potato protein and the remaining protein is plant protein.

In a preferred embodiment, 100% by weight of the total protein in the nutritional composition is potato protein.

Potato protein for use in the nutritional compositions of the invention is readily accessible or available, for example as concentrates or isolates, for example from commercial sources.

Potato protein may be extracted from potato tuber juice, which may itself be separated from potato solids by any of a number of suitable techniques known in the art. Chromatographic techniques may be used to purify potato proteins from the tuber juice in a similar manner to the isolation of milk proteins. Once isolated, the potato protein may be concentrated and subjected to temperature treatment and/or pH adjustment. Further steps may include, for example, removal of triglycoalkaloids, spray drying and/or UV treatment.

Suitable potato protein sources include complete potato protein extract (i.e. extract not subjected to fractionation by molecular mass); and potato protein fractionated by molecular mass, for example a high molecular mass fraction (e.g. greater than 35 kDa); or a low molecular mass fraction (e.g. less than 35 kDa). In one embodiment, the potato protein source is a low molecular mass potato protein fraction of less than 35 kDa.

The protein may be, for example, intact protein or hydrolysed protein (e.g. partially hydrolysed protein). Preferably, the protein is intact protein.

Hydrolysis of protein may in general be termed "partial" or "extensive" depending on the degree to which hydrolysis is carried out. Protein hydrolysates may have an extent of hydrolysis that is characterised by NPN/TN %, which refers to the non-protein nitrogen divided by the total nitrogen× 100. The non-protein nitrogen refers to amino nitrogen that is free to react with a reagent such as trinitrobenzenesulfonic acid (TNBS). NPN/TN % may be measured as described in Adler-Nissen (Adler-Nissen, J. (1979) J. Agric. Food Chem. 27: 1256-1262).

The term "extensive hydrolysis" may refer to hydrolysis that provides protein that has a NPN/TN % greater than 95%. The term "partial hydrolysis" may refer to hydrolysis that provides protein that has a NPN/TN % in the range 70-85%

In one embodiment, the protein has an NPN/TN % between 5-90%, 70-90% or 70-85%, preferably between 70-85%. In another embodiment, the protein has an NPN/TN % between 5-25% or 15-25%. In another embodiment, the protein has an NPN/TN % between 25-55%, 25-50% or 50-55%.

In one embodiment, 60-70% of the protein population has a molecular mass of less than 3000 Da.

In another embodiment, the protein has an NPN/TN % greater than 95%. These are "extensive" hydrolysates. In one embodiment, at least 95% of the protein population has a molecular mass of less than 3000 Da.

Proteins for use in the nutritional composition of the invention may be hydrolysed by any suitable method known in the art. For example, proteins may enzymatically hydrolysed, for example using a protease. For example, protein may be hydrolysed using alcalase.

Preferably, the proteins are hydrolysed by a method disclosed herein.

In one aspect, the invention provides a method of hydrolysis comprising the steps:
(i) providing a solution comprising potato protein, and optionally adjusting the pH of the solution to about 5.0-8.0, 5.0-7.6, 5.0-7.4, 6.0-7.6, 7.0-7.6 or 7.2-7.6, preferably 7.2-7.6;
(ii) adding a protease, preferably alcalase, to the solution of step (i);
(iii) incubating the solution of step (ii) under conditions suitable for hydrolysis of the potato protein; and
(iv) inactivating the protease.

In one embodiment, the incubation of step (iii) comprises adding the protease to provide an enzyme:substrate ratio of about 0.5-5% by weight.

In one embodiment, the incubation of step (iii) comprises incubating the solution at a temperature of about 50-70° C. or 55-60° C., preferably 55-60° C.

In one embodiment, the incubation of step (iii) is for about 0.5-5 h.

In one embodiment, the inactivation of step (iv) comprises heating the solution to about 85-95° C. or 88-92° C., preferably 88-92° C. Preferably, the solution is heated for at least about 5 minutes, for example about 5-30, 5-20, 5-15 or 5-10 minutes. Preferably, the solution is cooled to about 55-65° C. or 55-60° C., preferably 55-60° C., after the inactivation of step (iv).

Free Amino Acids

The nutritional compositions disclosed herein may further comprise free amino acids, i.e. free amino acids may be added during the method of the invention. Such free amino acids provide a protein equivalent source.

Free amino acids may be incorporated in the nutritional compositions disclosed herein to supplement the amino acids comprised in the protein. The levels of free amino acids may be chosen to provide an amino acid profile that is sufficient for nutrition of a specific subject, in particular an amino acid profile that satisfies nutritional regulations (e.g. European Commission Directive 2006/141/EC). Preferably, the levels of free amino acids are chosen to provide sufficient infant nutrition.

Example free amino acids for use in the nutritional compositions disclosed herein include histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof.

Carbohydrate

The carbohydrate content of the infant formula of the invention is preferably in the range 9-14 g carbohydrate per 100 kcal.

The carbohydrate may be any carbohydrate which is suitable for use in a nutritional composition, in particular an infant formula.

Example carbohydrates for use in the nutritional compositions disclosed herein include lactose, saccharose, maltodextrin and starch. Mixtures of carbohydrates may be used.

In one embodiment, the carbohydrate comprises maltodextrin. In one embodiment, at least 40%, 50%, 60% or 70% by weight of the total carbohydrate in the nutritional composition is maltodextrin.

In one embodiment, the carbohydrate comprises lactose. In one embodiment, at least 40%, 50%, 60% or 70% by weight of the total carbohydrate in the nutritional composition is lactose.

In one embodiment, the carbohydrate comprises lactose and maltodextrin.

Fat

The fat content of the infant formula of the invention is preferably in the range 4.0-6.0 g lipids per 100 kcal.

The fat may be any lipid or fat which is suitable for use in a nutritional composition, in particular an infant formula.

Example fats for use in the nutritional compositions disclosed herein include sunflower oil, low erucic acid rapeseed oil, safflower oil, canola oil, olive oil, coconut oil, palm kernel oil, soybean oil, fish oil, palm oleic, high oleic sunflower oil and high oleic safflower oil, and microbial fermentation oil containing long chain, polyunsaturated fatty acids.

The fat may also be in the form of fractions derived from these oils, such as palm olein, medium chain triglycerides and esters of fatty acids such as arachidonic acid, linoleic acid, palmitic acid, stearic acid, docosahexaeonic acid, linolenic acid, oleic acid, lauric acid, capric acid, caprylic acid, caproic acid, and the like.

Further example fats include structured lipids (i.e. lipids that are modified chemically or enzymatically in order to change their structure). Preferably, the structured lipids are sn2 structured lipids, for example comprising triglycerides having an elevated level of palmitic acid at the sn2 position of the triglyceride.

Oils containing high quantities of preformed arachidonic acid and/or docosahexaenoic acid, such as fish oils or microbial oils, may also be added.

Long chain polyunsaturated fatty acids, such as dihomo-γ-linolenic acid, arachidonic acid, eicosapentaenoic acid and docosahexaenoic acid, may be added. Willemsen et al. showed that the addition of such fatty acids supported epithelial barrier integrity and reduced IL-4 mediated permeability (Willemsen, L. E. et al. (2008) Eur. J. Nutr. 47: 183-91).

Structured lipids may be added or may be omitted. Medium chain triglycerides may be added or may be omitted.

Further Ingredients

The nutritional composition may contain some or all vitamins and minerals understood to be essential in the daily diet in nutritionally significant amounts. Minimum requirements have been established for certain vitamins and minerals.

Example vitamins, minerals and other nutrients for use in the nutritional composition include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine and L-carnitine.

Minerals are usually added in their salt form.

The nutritional composition may also comprise at least one probiotic. The term "probiotic" refers to microbial cell preparations or components of microbial cells with beneficial effects on the health or well-being of the host (Salminen, S. et al. (1999) Trends Food Sci. Technol. 10: 107-10). In particular, probiotics may improve gut barrier function (Rao, R. K. (2013) Curr. Nutr. Food Sci. 9: 99-107).

Preferred probiotics are those which as a whole are safe, are L(+) lactic acid producing cultures and have acceptable shelf-life for products that are required to remain stable and effective for up to 24 months.

Examples of probiotic micro-organisms for use in the nutritional composition include yeasts, such as *Saccharomyces, Debaromyces, Candida, Pichia* and *Torulopsis*; and bacteria, such as the genera *Bifidobacterium, Bacteroides, Clostridium, Fusobacterium, Melissococcus, Propionibacterium, Streptococcus, Enterococcus, Lactococcus, Staphylococcus, Peptostrepococcus, Bacillus, Pediococcus, Micrococcus, Leuconostoc, Weissella, Aerococcus, Oenococcus* and *Lactobacillus*.

Specific examples of suitable probiotic microorganisms are: *Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei* subsp. *casei, Lactobacillus casei Shirota, Lactobacillus curvatus, Lactobacillus delbruckii* subsp. *lactis, Lactobacillus farciminus, Lactobacillus gasseri, Lactobacillus helveticus, Lactobacillus johnsonii, Lactobacillus rhamnosus* (*Lactobacillus* GG), *Lactobacillus sake, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus* and *Staphylococcus xylosus*.

Preferred probiotic bacterial strains include *Lactobacillus rhamnosus*; *Lactobacillus rhamnosus* LPR (CGMCC 1.3724); *Bifidobacterium lactis* BL818 (CNCM 1-3446) sold inter alia by the Christian Hansen company of Denmark under the trade mark BB 12; and *Bifidobacterium longum* BL999 (ATCC BAA-999) sold by Morinaga Milk Industry Co. Ltd. of Japan under the trade mark BB536.

The nutritional composition may also contain other substances which may have a beneficial effect such as human milk oligosaccharides, prebiotics, lactoferrin, fibres, nucleotides, nucleosides and the like.

EXAMPLES

Example 1

Nutritional Comparison Between Potato Protein and Rice Protein

Figure 1:
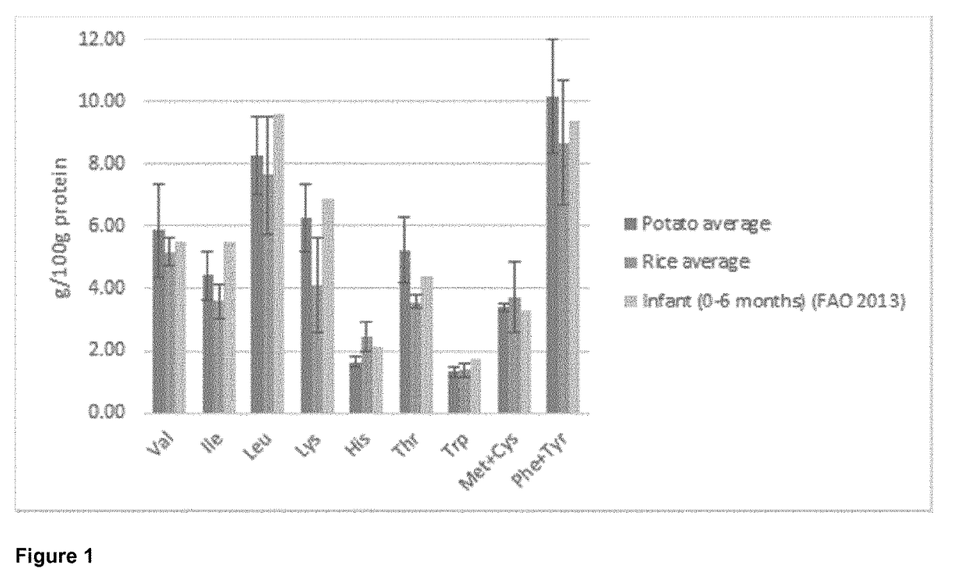
FIG. 1
Comparison of essential amino acid levels between potato and rice protein, and FAO 2013 recommendations.
Figure 2:
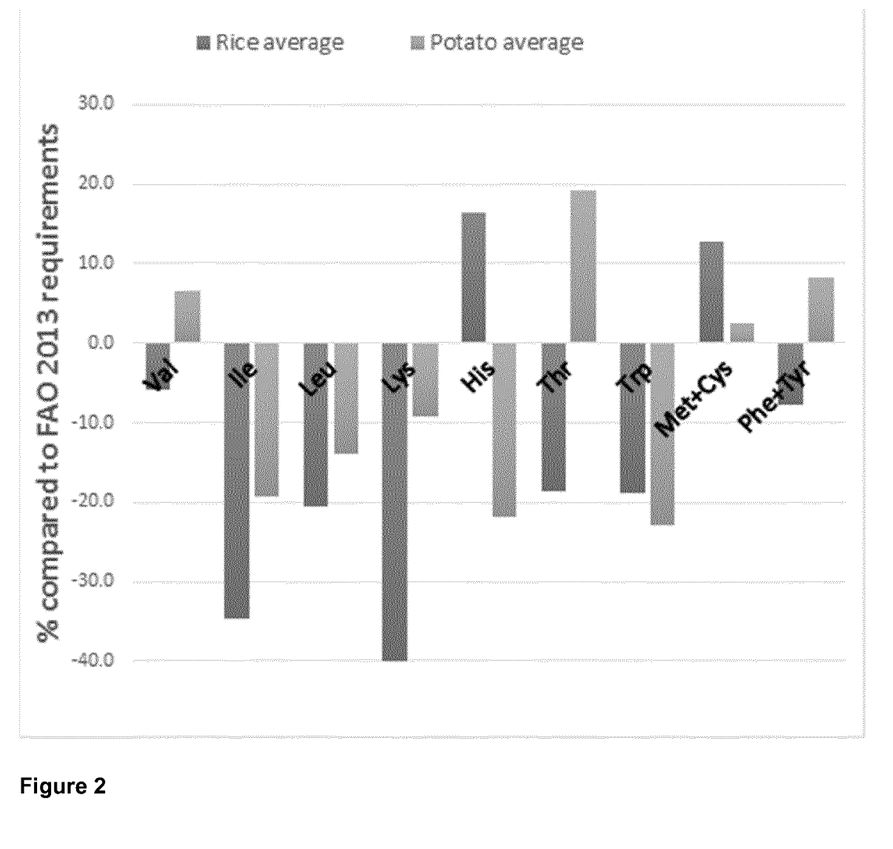
FIG. 2
Comparison of essential amino acid levels between potato and rice protein, and FAO 2013 recommendations.

Potato protein contains higher levels of the following essential amino acids compared to rice protein (FIGS. 1 and 2): valine; isoleucine; leucine; lysine; threonine and aromatic amino acids.

The concentrations of tryptophan and the sulphur-containing amino acids are similar between potato and rice proteins.

However, rice protein contains higher concentrations of histidine than potato protein.

Overall, the essential amino acid concentrations in potato protein are better than rice protein, and may require lower levels of additional amino acid fortification.

Potato protein contains more essential amino acids in compliance with the FAO 2013 recommendations compared to rice protein (Table 1).

TABLE 1

Amino acid concentrations in potato and rice proteins that are complaint with the FAO 2013 recommendations for 0-6 month-old infants.

| Amino acid | Potato | Rice |
| --- | --- | --- |
| Val | ✓ | x |
| Ile | x | x |
| Leu | x | x |
| Lys | x | x |
| His | x | ✓ |
| Thr | ✓ | x |
| Trp | x | x |
| Met + Cys | ✓ | ✓ |
| Phe + Tyr | ✓ | x |

Figure 3:
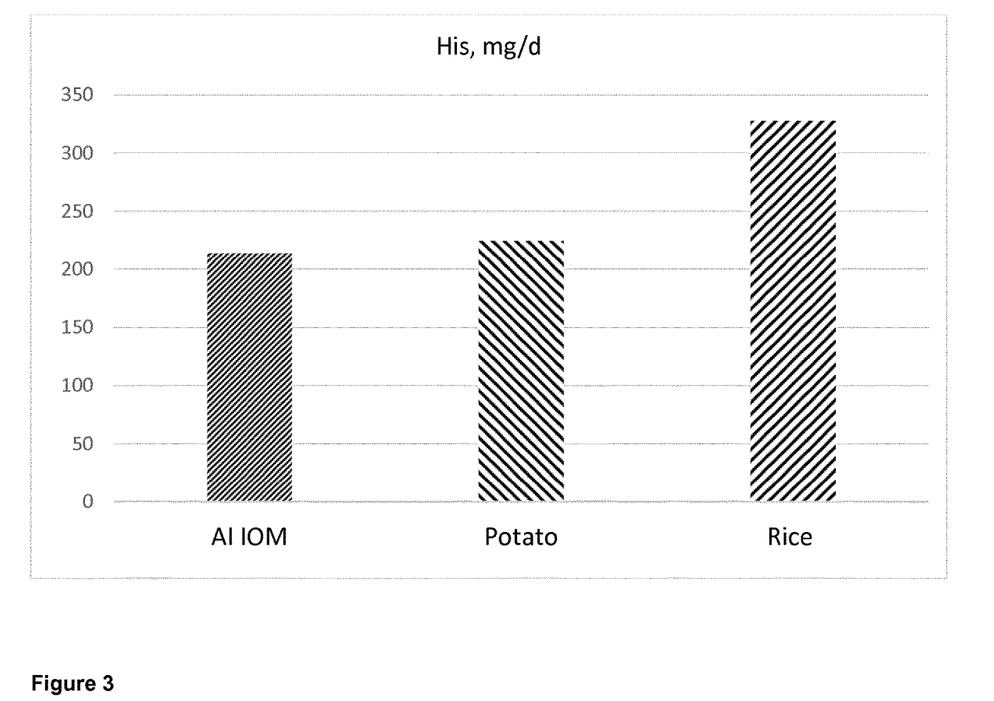
FIG. 3
Comparison of histidine levels between potato and rice protein, and Institute of Medicine of the National Academies recommendations (assuming an infant formula intake of 1000 mL per day, with a minimum of 1.8 g protein per 100 kcal for infants of 6 months of age (or 12.6 g protein per day)).

Although the levels of histidine are lower in potato protein than rice protein, and are lower than the FAO 2013 recommendations for 0-6 month-old infants, potato protein will still deliver histidine levels that are compliant with the 214 mg/d histidine suggested by Institute of Medicine of the National Academies Adequate Intake (AI) for 0-6 month-old infants (FIG. 3).

Figure 4:
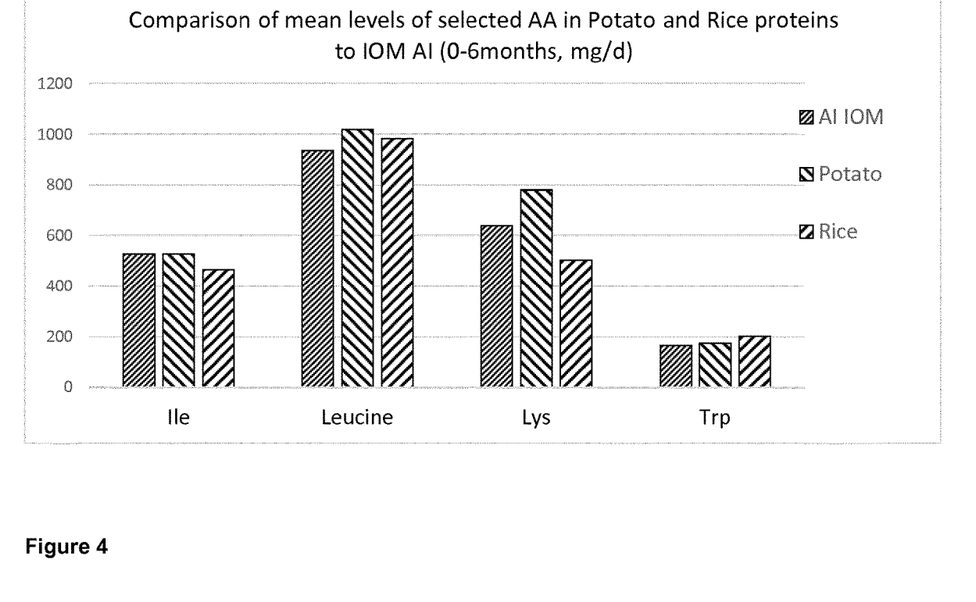
FIG. 4
Comparison of isoleucine, leucine, lysine and tryptophan levels between potato and rice protein, and Institute of Medicine of the National Academies recommendations (assuming an infant formula intake of 1000 mL per day, with a minimum of 1.8 g protein per 100 kcal for infants of 6 months of age (or 12.6 g protein per day)).

Furthermore, although the concentrations of isoleucine, leucine, lysine and tryptophan are lower in potato compared to the FAO 2013 recommendations, these levels are similar or higher than the levels in rice. Additionally, potato protein will meet the Institute of Medicine of the National Academies AI recommendations for these amino acids, while rice protein will not meet the recommendations for isoleucine and lysine (FIG. 4).

The concentrations for isoleucine, leucine and lysine taken from the supplier data indicates that the levels of these amino acids will be compliant with WHO 2007, 2013 and EC Directive 2006/141/EC, and codex standard (CODEX STAN 72-1981), in addition to Institute of Medicine of the National Academies AI recommendations.

Branched-Chain Amino Acids (BCAA)

Branched-chain amino acids (BCAA; leucine, isoleucine and valine) have an important role in protein synthesis. Leucine is an activator of mTOR, and promotes protein synthesis and suppress protein catabolism, resulting in maintenance of muscle protein during restricted dietary intake. Children with food allergies follow dietary restrictions, therefore they are at risk of developing malnutrition, hence consumption of plant protein with high levels of BCAAs may help maintain muscle proteins.

Figure 5:
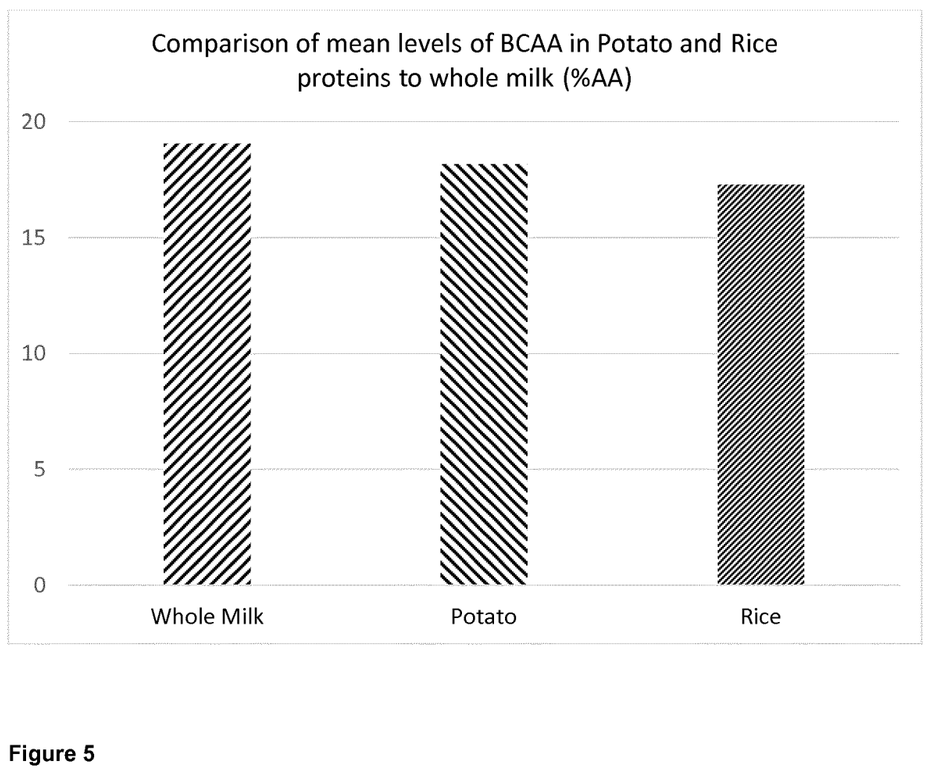
FIG. 5
Comparison of branched-chain amino acid (BCAA) levels between potato and rice protein, and whole milk.

Additionally, the best food sources of BCAAs are meat, fish, dairy products and eggs, which may not be consumed at all, or at least consumed in smaller amounts by infants and small children with food allergies. FIG. 5 shows that the sum of BCAA (% AA) in potato is closer to that in milk and therefore provides an advantage to children with cow's milk protein allergy. Accordingly, providing a protein source with higher levels of BCAAs may benefit this paediatric population.

Lysine and Threonine

Figure 6:
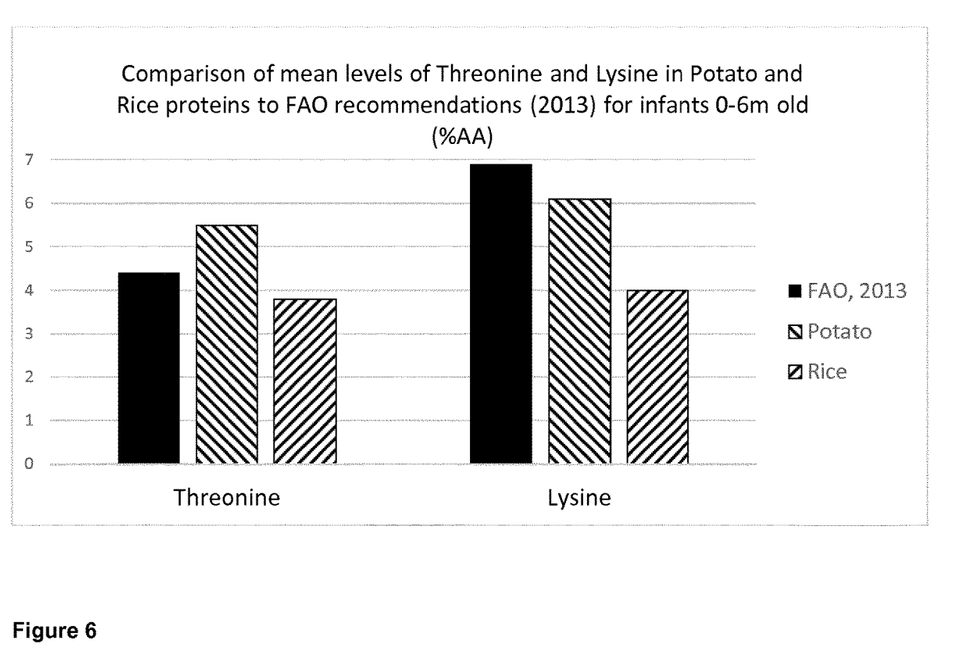
FIG. 6
Comparison of mean levels of threonine and lysine between potato and rice protein, and FAO 2013 recommendations.

Lysine and threonine are the first and second most limiting amino acids, respectively, for protein synthesis in human subjects consuming a predominantly cereal-based diet such as wheat and rice. The main roles of lysine and threonine are in protein synthesis. Unlike other plant proteins sources such as rice and wheat proteins, potato protein has higher levels of these two amino acids, with lysine levels close to the requirement set by the FAO 2013 recommendations and threonine levels exceeding it (FIG. 6).

The best food sources of threonine and lysine are soy, dairy products, nuts, and fish, beef or chicken. These food sources may not be consumed at all, or at least consumed in smaller amounts by infants and small children with food allergies. Therefore providing a non-animal source of protein with high concentrations of these two amino acids will benefit this paediatric population.

Aromatic Amino Acids

Phenylalanine is a precursor for tyrosine, the neurotransmitters dopamine, norepinephrine, and adrenaline, and the skin pigment melanin. Potato protein exceeds the requirements set by the FAO 2013 recommendations for 0-6 month-old infants, while rice does not meet the recommended level.

Figure 7:
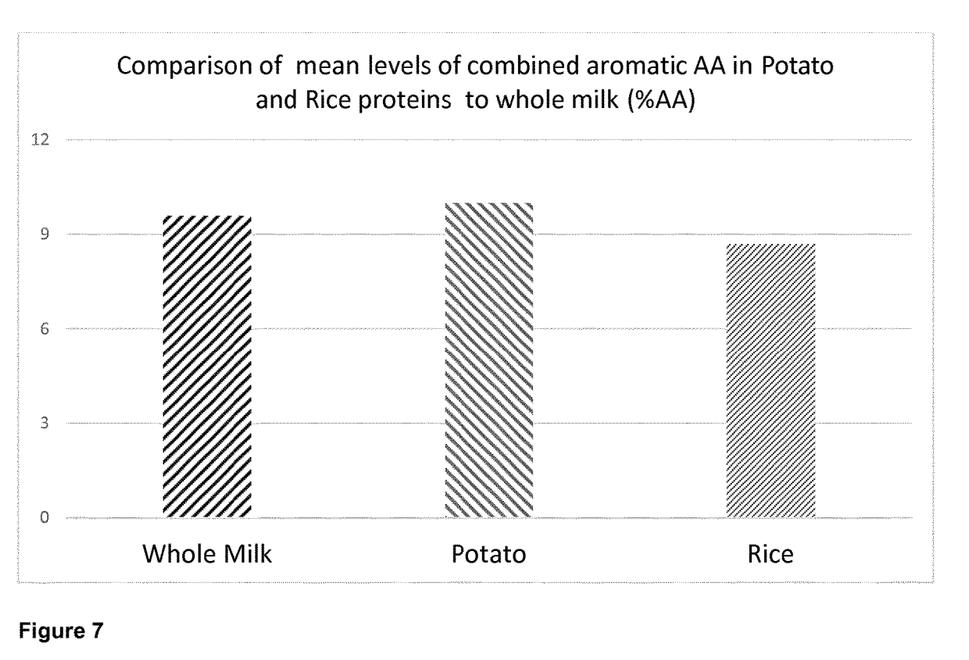
FIG. 7
Comparison of mean levels of combined aromatic amino acids between potato and rice protein, and whole milk.

The best food sources of phenylalanine are eggs, chicken, liver, beef, milk and soybeans. These food sources may not be consumed at all, or at least consumed in smaller amounts by infants and small children with food allergies. However, the combined levels of phenylalanine and tyrosine in potato protein are similar to those in milk (FIG. 7), which provides an advantage to infants and children with cow's milk protein allergy.

Example 2

Methods of manufacturing nutritional compositions comprising potato protein with differing processes for addition of the minerals were compared.

The data in Table 2 show that the order of the addition of the minerals during the process of producing the nutritional composition has a significant effect on the viscosity of the liquid product. Optimising this order makes it possible to achieve viscosities which improve spray drying and the quality of the spray-dried powder product.

Specifically, it was found that adding some minerals (e.g. calcium citrate and/or potassium citrate, and optionally sodium citrate and/or potassium phosphate monobasic) to the solution before the potato protein was beneficial in terms of the viscosity of the resulting solution. Other minerals (e.g. magnesium chloride, magnesium oxide, calcium chloride, calcium glycerophosphate and/or sodium chloride, and optionally calcium phosphate, potassium hydroxide and/or sodium hydroxide) could be added after the potato protein (this protocol is annotated as "minerals before and after" in Table 1).

In addition, it was found that adding all the minerals before the protein was also beneficial (this protocol is annotated as "minerals before" in Table 1).

Adjusted the pH back to 6.0 before and after homogenisation was not found to influence the viscosity or particle size (PSD).

TABLE 2

Analysis of viscosity and particle size.

| Sample | viscosity/ 100 | 200 | 300 | average | Total solids | PSD (d 0.5) um |
|---|---|---|---|---|---|---|
| >35 kDa potato protein fraction (minerals after) | 253 | 158 | 120 | 177 | 30.2 | 18.44 |
| <35 kDa potato protein fraction(minerals after) | 132 | 74 | 54 | 87 | 28.2 | 12.26 |
| >35 kDa potato protein fraction (minerals before and after) | 94 | 54 | 40 | 63 | 28.8 | 43.65 |
| <35 kDa potato protein fraction (minerals before and after) | 45 | 31 | 23 | 33 | 29.4 | 13.33 |
| Full range potato protein (i.e. no molecular mass-based fractionation) (minerals after) | 280 | 156 | 113 | 183 | 30.1 | 36.60 |
| <35 kDa potato protein fraction (minerals before and after) | 439.7 | 289 | 223 | 317 | 55 | 12.39 |
| <35 kDa potato protein fraction (minerals before) | 23 | 17 | 14 | 18 | 27.8 | 28.39 |
| <35 kDa potato protein fraction (minerals before) pH 6 before homogenisation | 11 | 10 | 10 | 10 | 25.6 | 24.17 |
| <35 kDa potato protein fraction (minerals before) pH 6 after homogenisation | 10 | 9 | 9 | 9 | 25.6 | 20.75 |

All publications mentioned in the above specification are herein incorporated by reference. Various modifications and variations of the described compositions and methods of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention, which are obvious to those skilled in biochemistry and biotechnology or related fields, are intended to be within the scope of the following claims.

The invention claimed is:

1. A method for producing a nutritional composition, the method comprising:
   (a) providing a solution comprising a first mineral selected from the group consisting of calcium citrate, potassium citrate, potassium phosphate monobasic, and mixtures thereof;

(b) adding at least one potato protein to the solution of step (a);
(c) adding at least one carbohydrate and/or at least one fat to the solution of step (b); and
(d) spray drying the solution of step (c).

2. The method of claim 1 comprising stirring the solution of steps (a) and/or (b).

3. The method of claim 1, wherein step (a) further comprises adjusting a pH of the solution to about 3.8-7.0 before addition of the at least one potato protein in step (b).

4. The method of claim 1, wherein step (c) further comprises adjusting a pH of the solution to about 3.8-7.0 after addition of the at least one carbohydrate.

5. The method of claim 1, wherein the method does not comprise a homogenisation step.

6. The method of claim 1, wherein the nutritional composition is an infant formula.

7. The method of claim 1, wherein the solution of step (a) comprises a second mineral selected from the group consisting of sodium citrate, magnesium chloride, magnesium oxide, calcium chloride, calcium glycerophosphate, sodium chloride, calcium phosphate, potassium hydroxide, sodium hydroxide, and mixtures thereof.

8. The method of claim 1, wherein step (c) further comprises adding a third mineral and/or a vitamin.

9. The method of claim 8, wherein the third mineral added in step (c) is selected from the group consisting of magnesium chloride, magnesium oxide, calcium chloride, calcium glycerophosphate, potassium phosphate monobasic, sodium chloride, calcium phosphate, potassium hydroxide, sodium citrate, sodium hydroxide, and mixtures thereof.

10. The method of claim 1, wherein step (c) comprises adding the at least one carbohydrate before the at least one fat.

11. The method of claim 1, wherein the at least one potato protein comprises hydrolyzed potato protein.

12. The method of claim 11, wherein the hydrolysed potato protein is produced by a process comprising:
providing a solution comprising potato protein;
(ii) adding a protease to the solution of step (i);
(iii) incubating the solution of step (ii) under conditions suitable for hydrolysis of the potato protein; and
(iv) inactivating the protease.

13. The method of claim 12, wherein the incubation of step (iii) comprises incubating the solution of step (ii) at a temperature of about 55-60° C. for about 0.5-5 h.

14. The method of claim 12, wherein step (i) further comprises adjusting the pH of the solution to about 5.0-8.0.

15. The method of claim 12, wherein the protease added in step (ii) comprises alcalase.

16. The method of claim 1, wherein the first mineral comprises calcium citrate and/or potassium phosphate monobasic.

17. The method of claim 8 wherein step (c) further comprises adding a fourth mineral selected from the group consisting of sodium citrate, magnesium chloride, magnesium oxide, calcium chloride, calcium glycerophosphate, potassium phosphate monobasic, sodium chloride, calcium phosphate, potassium hydroxide, sodium hydroxide, and mixtures thereof.

* * * * *